(12) United States Patent
Trauba

(10) Patent No.: US 11,192,103 B2
(45) Date of Patent: Dec. 7, 2021

(54) MICRO-FLUIDIC DEVICE FOR RAPID PCR

(71) Applicant: UNIVERSITY OF UTAH RESEARCH FOUNDATION, Salt Lake City, UT (US)

(72) Inventor: James Trauba, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 129 days.

(21) Appl. No.: 16/609,073

(22) PCT Filed: May 3, 2018

(86) PCT No.: PCT/US2018/030814
§ 371 (c)(1),
(2) Date: Oct. 28, 2019

(87) PCT Pub. No.: WO2018/204592
PCT Pub. Date: Nov. 8, 2018

(65) Prior Publication Data
US 2020/0055049 A1 Feb. 20, 2020

Related U.S. Application Data

(60) Provisional application No. 62/501,171, filed on May 4, 2017.

(51) Int. Cl.
*B01L 7/00* (2006.01)
*C12Q 1/686* (2018.01)
*B01L 3/00* (2006.01)

(52) U.S. Cl.
CPC ......... *B01L 3/502715* (2013.01); *B01L 7/525* (2013.01); *C12Q 1/686* (2013.01);
(Continued)

(58) Field of Classification Search
CPC ..... B01L 2300/0816; B01L 2300/0883; B01L 3/502715; B01L 7/525; B01L 2200/147;
(Continued)

(56) References Cited

U.S. PATENT DOCUMENTS 6,755,211 B1 6/2004 O'Connor et al.
6,827,095 B2 12/2004 O'Connor et al.
(Continued)

FOREIGN PATENT DOCUMENTS

CN 106065391 A 11/2016
WO WO-0189692 A2 * 11/2001 ............ B01F 5/0057
WO 2016/140990 A1 9/2016

OTHER PUBLICATIONS

International Search Report and Written Opinion issued in PCT/US2018/030814 dated Jul. 12, 2018.
(Continued)

*Primary Examiner* — Young J Kim
(74) *Attorney, Agent, or Firm* — Workman Nydegger

(57) ABSTRACT

The present disclosure describes systems and devices capable of providing rapid polymerase chain reaction processes. A microfluidic card is insertable into a heating assembly. The heating assembly provides separate temperature zones to the card. The card includes a channel array that traverses repeatedly through the separate temperature zones so that a reaction mixture passing through the channel is subjected to thermal cycling.

25 Claims, 9 Drawing Sheets

(52) U.S. Cl.
CPC . *B01L 2200/147* (2013.01); *B01L 2300/0816* (2013.01); *B01L 2300/0883* (2013.01); *B01L 2300/1805* (2013.01)

(58) Field of Classification Search
CPC ..... B01L 2300/0663; B01L 2300/1805; C12Q 1/686
See application file for complete search history.

(56) References Cited

U.S. PATENT DOCUMENTS

| | | |
|---|---|---|
| 7,030,340 B2 | 4/2006 | Jochem |
| 7,964,139 B2 | 6/2011 | Liu et al. |
| 8,053,215 B2 | 11/2011 | Hwang et al. |
| 9,205,396 B2 | 12/2015 | Susumu |
| 2009/0317874 A1 | 12/2009 | Dale et al. |
| 2013/0217022 A1 | 8/2013 | Cao et al. |
| 2014/0179909 A1 | 6/2014 | O'Halloran et al. |
| 2014/0206562 A1 | 7/2014 | McCormack et al. |
| 2015/0118715 A1 | 4/2015 | Wittwer et al. |
| 2015/0376692 A1 | 12/2015 | Esfandyarpour et al. |

OTHER PUBLICATIONS

Ross et al. "Microfluidic Temperature Gradient Focusing" Anal. Chem, 2002, vol. 74, pp. 2556-2564.

\* cited by examiner

Position

MICRO-FLUIDIC DEVICE FOR RAPID PCR

CROSS-REFERENCE TO RELATED APPLICATIONS

This application is a U.S. National Stage Application of PCT/US2018/030814 filed May 3, 2018, entitled MICROFLUIDIC DEVICE FOR RAPID PCR, which claims the benefit of and priority to U.S. Provisional Patent Application No. 62/501,171, filed on May 4, 2017, entitled MICROFLUIDIC DEVICE FOR RAPID PCR, the entireties of which are incorporated herein by this reference.

BACKGROUND

Polymerase Chain Reaction (PCR) is an inexpensive and robust technique for amplifying specific segments of DNA by several orders of magnitude. PCR methods rely on thermal cycling of the constituent reactants through multiple cycles of heating and cooling to permit separate temperature-dependent reactions to proceed. The speed (i.e., cycle time) at which PCR can be performed is largely determined by the time required to cycle through the temperature dependent steps of DNA denaturation, primer annealing, and polymerase extension.

Limitations to PCR remain, however. In particular, conventional PCR technology has not kept pace with the rising need for higher throughput and higher speeds. Accordingly, there is an ongoing need for improved PCR devices, systems, and related methods that are capable of improving the speed and/or throughput of PCR.

BRIEF SUMMARY

The present disclosure describes systems and devices capable of performing rapid PCR. An exemplary embodiment includes a heating assembly configured for receiving a microfluidic card. The microfluidic card is configured in size and shape so as to be insertable within the heating assembly. When inserted, the heating assembly provides differential heat to different sections of the card such that a plurality of different temperature zones are formed on the card. The microfluidic card includes an inlet for receiving a reaction mixture (e.g., sample, primers, dNTPs, polymerase, buffer, etc.), and a channel array that directs a received reaction mixture repeatedly through the separate temperature zones. The reaction mixture is thereby subjected to thermal cycling to enable PCR and DNA amplification to occur.

In one embodiment, the microfluidic card includes a longitudinal axis, an upper surface, a lower surface, and an inlet for providing access to an internal channel. The internal channel extends in a serpentine pattern to form a plurality of lateral sections that are oriented transverse to the longitudinal axis such that a fluid passing through the channel array passes through the lateral sections as it moves downstream of the inlet. When such a card is inserted into a corresponding heat assembly, the repeated passage of the fluid across a width of the card as it moves through the lateral sections moves the fluid repeatedly through separate temperature zones to provide thermal cycling of the fluid.

Additional features and advantages will be set forth in part in the description that follows, and in part will be obvious from the description, or may be learned by practice of the embodiments disclosed herein. The objects and advantages of the embodiments disclosed herein will be realized and attained by means of the elements and combinations particularly pointed out in the appended claims. It is to be understood that both the foregoing brief summary and the following detailed description are exemplary and explanatory only and are not restrictive of the embodiments disclosed herein or as claimed.

BRIEF DESCRIPTION OF THE DRAWINGS

In order to describe various features and concepts of the present disclosure, a more particular description of certain subject matter will be rendered by reference to specific embodiments which are illustrated in the appended drawings. Understanding that these figures depict just some example embodiments and are not to be considered to be limiting in scope, various embodiments will be described and explained with additional specificity and detail through the use of the accompanying drawings in which.

DETAILED DESCRIPTION

Figure 1:
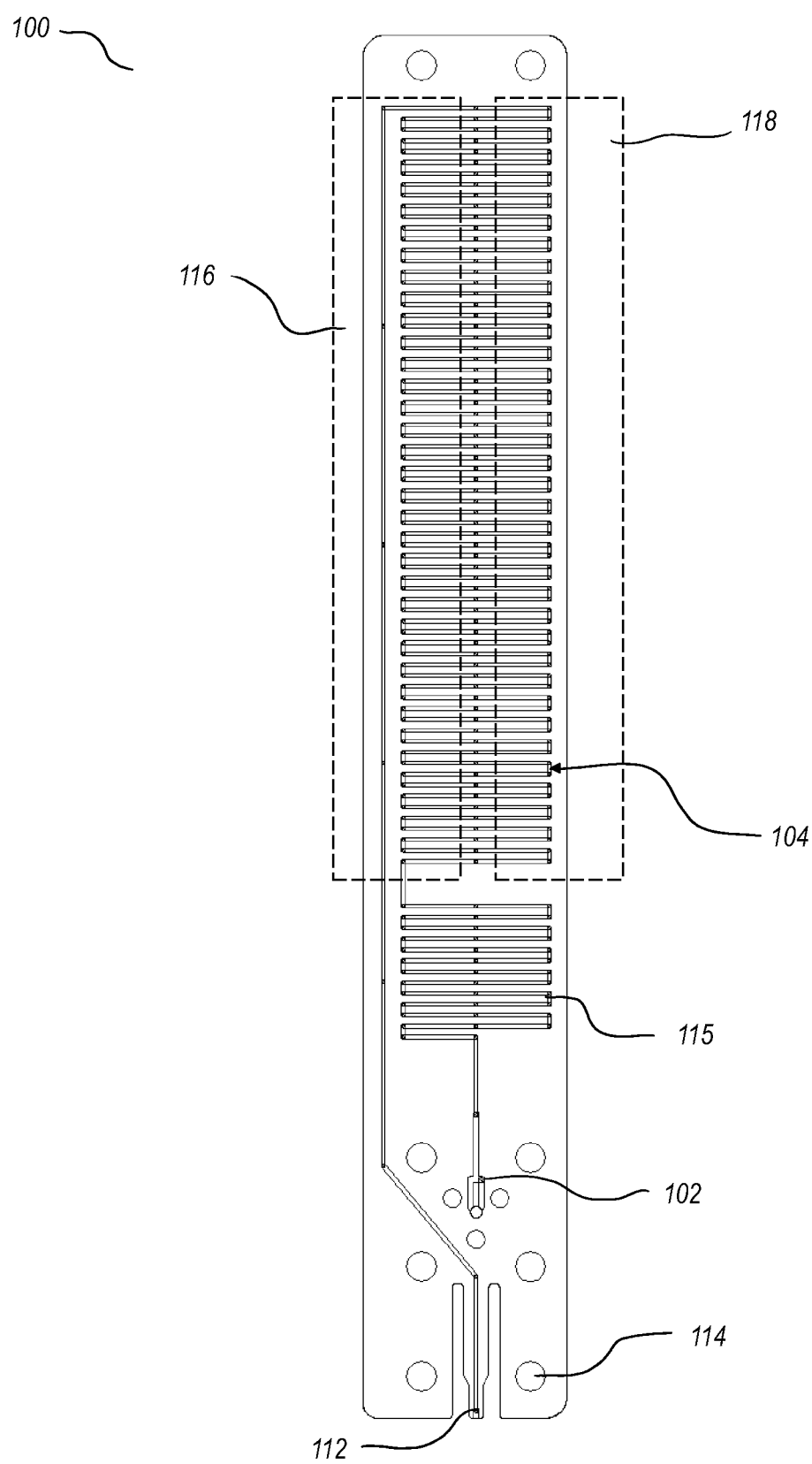
FIG. 1 illustrates a microfluidic card according to one exemplary embodiment.

FIG. 1 illustrates an exemplary embodiment of a rapid PCR card which may be utilized in a rapid PCR device as described herein. As described in more detail below, the card is configured in size and shape to be insertable into a heating assembly. The heating assembly is configured to provide differential heating to different sections of the card to form separate temperature zones 116 and 118.

As shown, the card includes an inlet 102 capable of fluid communication with an interior channel array 104. In the illustrated embodiment, the channel array 104 is formed in a winding, serpentine pattern that repeatedly passes through the separate temperature zones 106 and 108 as the channel longitudinally extends away from the inlet 102. As used herein, each length of the channel array 104 passing from one temperature zone to the next is referred to as a "lateral section" or a "lateral pass" while the overall extension from the inlet side of the card toward the opposite side of the card is referred to as a "longitudinal section" or a "longitudinal pass."

When a PCR mixture is passed into and through the channel array 104, the resulting fluid plug will follow the channel path through the multiple lateral passes and through the separate temperature zones 116 and 118. Under laminar or substantially laminar flow conditions, a given segment of the fluid plug will thus be repeatedly cycled between the temperatures of the separate temperature zones 116 and 118.

Alternative embodiments may include a channel array formed in a different pattern. For example, the channel array may be formed in a helical/spiral pattern, a zig-zag pattern, or the like. Although the illustrated channel array 104 represents one exemplary embodiment, other patterns capable of directing a fluid repeatedly across separate temperature zones may also be utilized.

As shown, the illustrated microfluidic/PCR card 100 includes two temperature zones for carrying out rapid PCR, with a first temperature zone 116 (i.e., the relatively "hot" zone) being configured for the DNA denaturization step (e.g., at about 90° C.) and a second temperature zone 118 (i.e., the relatively "cold" zone) being configured for the annealing and extension steps (e.g., at about 65° C.). Alternative embodiments may include additional temperature zones to further refine the PCR process according to particular application needs. For example, some embodiments may include a first temperature zone particularly tailored to the DNA denaturization step, a second temperature zone particularly tailored to the annealing step, and a third temperature zone particularly tailored to the extension step. The particular temperatures at which such zones may be set for carrying out the respective PCR steps is well understood in the art.

The illustrated card includes an outlet 112 for withdrawing the fluid plug and/or other fluids from the channel array 104. The card may also include one or more alignment marks and/or indexing features 114 for aligning the card with heating blocks, a clamping mechanism, a pneumatic device or pump, other components of the rapid PCR system, manufacturing equipment (e.g., heat press), and/or other components of a rapid PCR system. The indexing features 114 may be formed as holes configured for receiving matching pins, for example.

As described in more detail below, the card 100 is formed with thin walls to enable effective heat transfer from the heating assembly to the fluid plug within the channel array 104. The thin walls thereby promote rapid heat transfer and greater temperature uniformity (i.e., less of a temperature gradient) within the discrete temperature zones. Greater temperature uniformity promotes more defined and more stable temperature zones, which enables better overall PCR results (e.g., greater and/or faster amplification of template/target DNA).

In some embodiments, the card has a wall thickness that is less than 1 mm. For example, the wall thickness may be about 500 µm or less, may be about 300 µm or less, may be about 150 µm or less, may be about 75 µm or less, may be about 50 µm or less, or may be as low as about 12.5 to 25 µm. In some embodiments, the wall thickness is within a range with endpoints defined by any two of the foregoing values. In some embodiments, the wall thickness may be even less, with thinner walls being preferred as far as manufacturability, structural integrity, and production economics allow.

In some embodiments, the overall thickness of the card is about 750 µm or less, about 500 µm or less, about 250 µm or less, about 50 to 100 µm. In some embodiments, the card has a thickness within a range having endpoints defined by any two of the foregoing values.

The illustrated embodiment also includes a set of inlet turns 115 arranged downstream of the inlet 102 and upstream from the temperature zones 116 and 118. The inlet turns 115 help to modulate and normalize fluid flow to ensure constant flow rate and cycle time once the fluid plug reaches the temperature zones 116 and 118. The set of inlet turns 115 may include, for example, about 2 to 10 pairs of turns, or about 4 to 8 pairs of turns.

The card may be sized according to particular application needs and/or DNA amplification requirements. An exemplary embodiment may have a width of about 0.5 to 2 inches and a length of about 5 to 9 inches, with about 50% to 90% of that length including the channel array 104 and separate temperature zones 116 and 118. Other embodiments may have other dimensional configurations. For example, as described in more detail below with respect to FIG. 7, some microfluidic cards may be manufactured with a lower length to width ratio while still providing a similar number of PCR cycles due to an alternative arrangement of the channel array.

Figure 2:
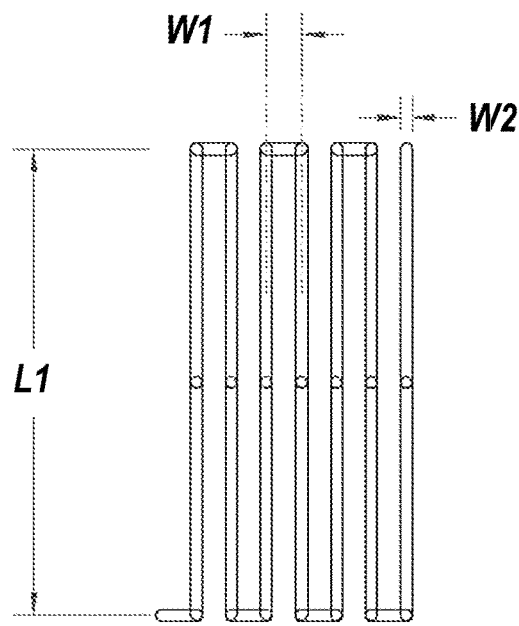
FIG. 2 illustrates a section of a channel array of the card of FIG. 1.

FIG. 2 illustrates a schematic view of a portion of the channel array 104. In some embodiments, each lateral section of the channel array 104 may have a length (L1) of about 10 to 30 mm (e.g., about 20 mm), each turn section may have a length (W1) of about 0.5 to 3 mm (e.g., about 1.5 mm), and the channel width (W2) may be about 0.2 to 1 mm (e.g., about 0.5 mm). Alternative embodiments may vary such dimensions according to expected fluid plug volume, fluid flow rate, number of temperature zones used, desired residence times within the different temperature zones, targeted cycle rate, desired number of thermal cycles, and/or other application needs. In particular, for a given fluid plug volume, the channel array dimensions should be arranged to avoid overextending the fluid plug and introducing excessive fluidic resistance. For a typical fluid plug volume of about 10 to 15 µl, channel array dimensions within the foregoing values have been found to provide effective results.

Figure 3:
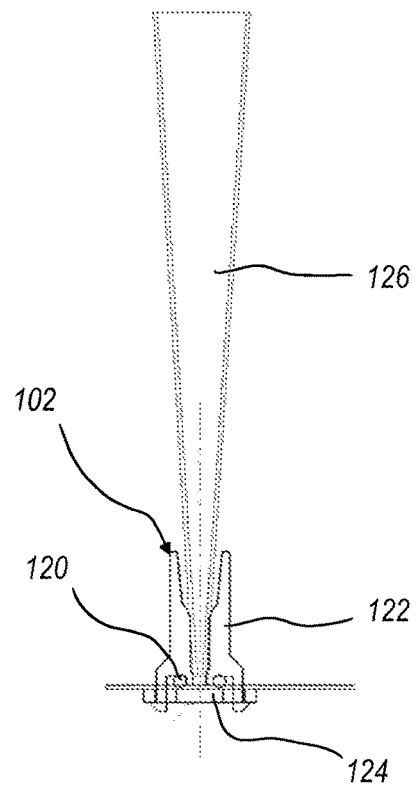
FIG. 3 illustrates an inlet of the card of FIG. 1.

FIG. 3 illustrates an expanded view of the inlet 102. As shown, the inlet 102 may include an O-ring 120 or other suitable seal to separate the interior of the channel array from the exterior environment. In the illustrated embodiment, the O-ring 120 is compressed between a connector 122 and a backing plate 124. Other embodiments may additionally or alternatively utilize one or more differently configured valves, gaskets, manifolds, or other sealing components. The connector 122 is configured to receive a fluid and direct it toward the O-ring 120. In a preferred embodiment, the connector 122 is configured in size and shape to receive a standard laboratory pipette tip 126, as shown.

In the illustrated embodiment, the connector 122 extends from the card so that the pipette tip 126 (or other suitable delivery structure) may be oriented at a substantially perpendicular angle relative to the longitudinal axis of the card. Such a configuration can enable ready access and use of the inlet 102 while the card is horizontally positioned. For example, the orientation of the inlet 102 allows a user to hold a pipette in the proper upright position while delivering a PCR mixture to the inlet 102.

Figure 4:
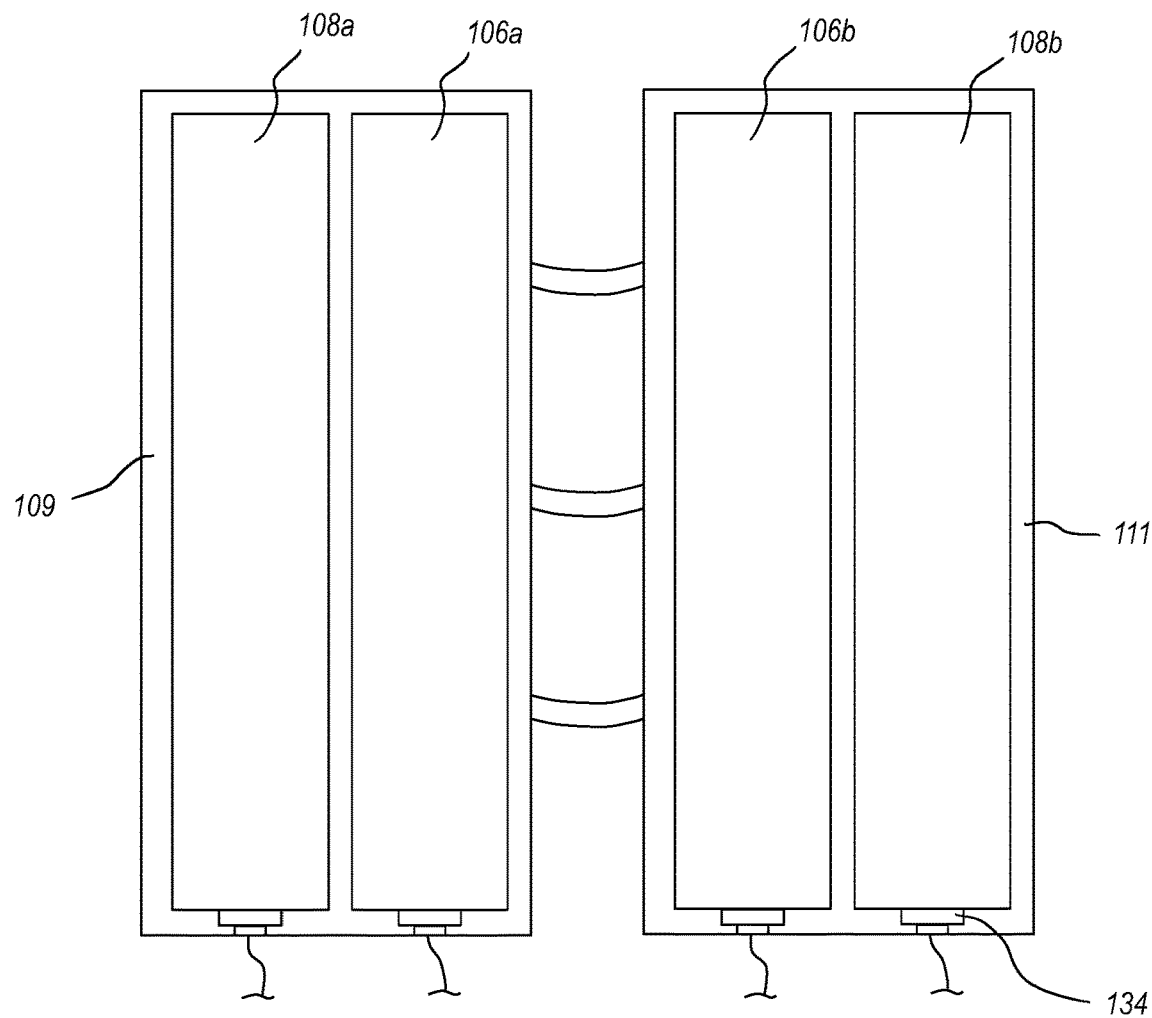
FIGS. 4 and 5 illustrate a heating assembly in which the card of FIG. 1 may be positioned and which may be operated to form separate temperature zones within the card.
Figure 5:
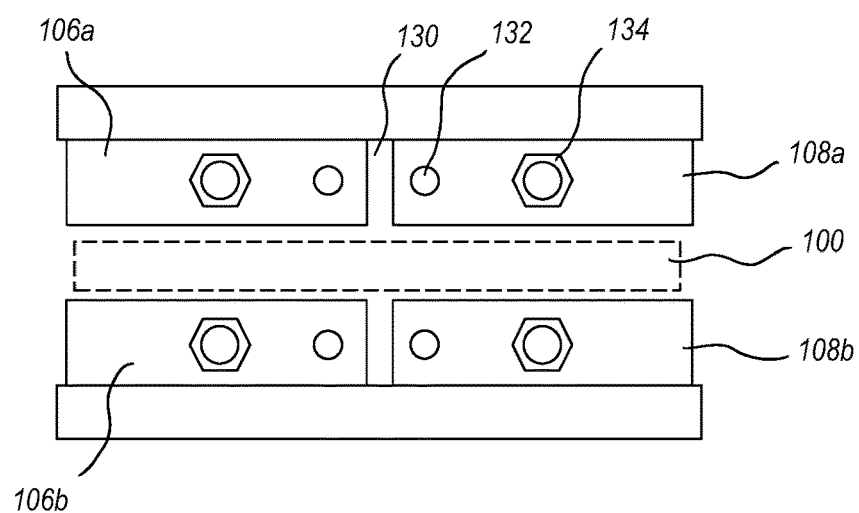

FIGS. 4 and 5 illustrate an exemplary heat assembly in which the card 100 (and/or other card embodiments described herein) may be inserted. FIG. 4 shows a top view of the heating assembly in an open configuration to better illustrate interior components of the heat assembly, and FIG. 5 illustrates a front view of the heat assembly in a closed configuration showing the manner in which the card 100 may be inserted. As shown, the "hot" zone (i.e., the denaturization zone) results from two corresponding blocks 106a and 106b, and the "cold" zone (i.e., the annealing/extension zone) is formed from two corresponding blocks 108*a* and 108*b*. As best shown in FIG. 5, when the heating assembly is closed, the blocks 106*a* and 106*b* are aligned on opposite sides of the card-receiving space to form the cold temperature zone, and the blocks 108*a* and 108*b* are aligned on opposite sides of the card-receiving space to form the hot temperature zone.

The microfluidic card 100 may be positioned within the card-receiving space so as to be "sandwiched" between the opposing sets of heating blocks. Such a configuration ensures that, for each temperature zone on the card, heat is applied from each side of the card. Relative to a single-sided heating arrangement, this beneficially reduces temperature gradients within the channels of the card and leads to greater temperature uniformity and improved PCR performance.

The blocks may be formed from any material with suitable thermal properties, such as copper, aluminum, or alloys thereof. The blocks may also be arranged to form a gap 130 between temperature zones, as shown. The gap 130 may function to better separate and define the different temperature zones. As shown, the blocks include one or more heating elements 134 for heating the blocks, and may include one or more sensor apertures 132 for coupling sensors (such as a resistance temperature detector).

A heating assembly and one or more microfluidic cards may together form a rapid PCR system. Such a rapid PCR system may additionally include a clamping fixture for compressing and fixing the blocks of the heating assembly against the card. Other embodiments may additionally or alternatively utilize other fastening mechanisms for securing the blocks of the heating assembly against the card. For example, in some embodiments the heating assembly may open along a hinge (to a position similar to that shown in FIG. 4) and/or may include a clasp or other locking mechanism for closing the assembly. In another example, the heating assembly may be pre-formed or pre-shaped into the intended closed configuration, with the PCR card sized to slide into and out of the receiving space (e.g., with a friction fit).

The rapid PCR system may additionally include a pneumatic assembly configured to be operatively coupled to the inlet 102. The pneumatic assembly may be configured to provide a pressure differential to move the fluid plug through the channel array 104. The pneumatic assembly may include a pneumatic head, pump, tubing, valves, regulator, manifold, or other suitable pneumatic components known in the art for providing the necessary operational pressures. Pressure application may vary according to channel geometry, volume of reaction mixture, and/or application needs. For a card having the channel geometries exemplified herein, and for a reaction mixture volume of about 10 to 15 µl, an applied pressure of about 1.5 to 5 psi, or about 3 psi, has shown effective results.

Figure 6:
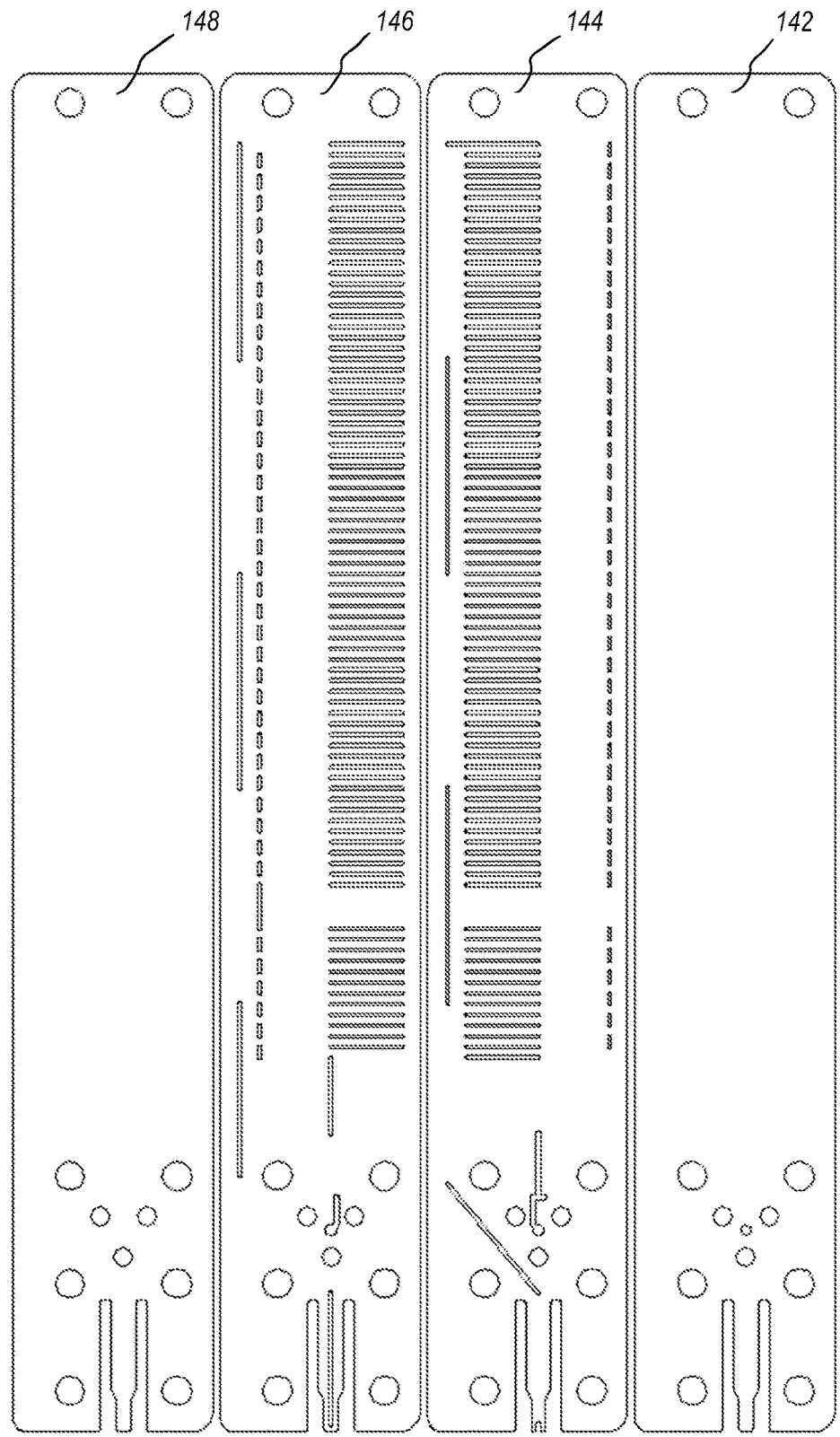
FIG. 6 illustrates the card of FIG. 1 in a layer-by-layer view.

FIG. 6 illustrates the card 100 showing layer-by-layer construction according to one embodiment of manufacture, with a first (top) layer 142, second layer 144, third layer 146, and fourth (bottom) layer 148. The microfluidic channels may be cut into the second and third layers 144 and 146 using xerography or other suitable micro-fabrication method. As shown, channel segments may alternate between layers at turning points and at intermediate positions within lateral segments, which beneficially prevents failures and channel inconsistency due to misalignment and/or cutting errors. The card 100 may alternatively be formed using other manufacturing methods, such as a photolithography-based method described in further detail below with respect to FIG. 8.

The card 100 is preferably formed from a material that is thermally bondable. For example, the illustrated layers 142, 144, 146, and 148 may be aligned and thermally bonded to form the completed card. Alternative embodiments may additionally or alternatively utilize adhesive coupling between layers. Suitable materials include polymers, and in particular thermoplastic polymers, such as polycarbonate, polymethyl methacrylate (PMMA), nylon, polyether sulfone (PES), poly ether ether ketone (PEEK), polyethylene (PE), polypropylene (PP), polyethylene terephthalate (PET), and combinations thereof, for example. The material(s) utilized to form the card 100 are preferably optically transparent to enable fluorescence measurements of the reaction mixture during a rapid PCR operation using the card 100.

Embodiments described herein are beneficially able to provide rapid PCR while also maintaining effective amplification efficiency. As used herein, "rapid PCR" refers to PCR cycle times of about 5 seconds or less, about 3 seconds or less, about 2 seconds or less, or as low as about 0.5 to 1 second per cycle. In addition, the thin film design of the card allows for a readily usable and inexpensive container for receiving samples that does not detrimentally impede heat transfer to the internal fluid.

Figure 7:
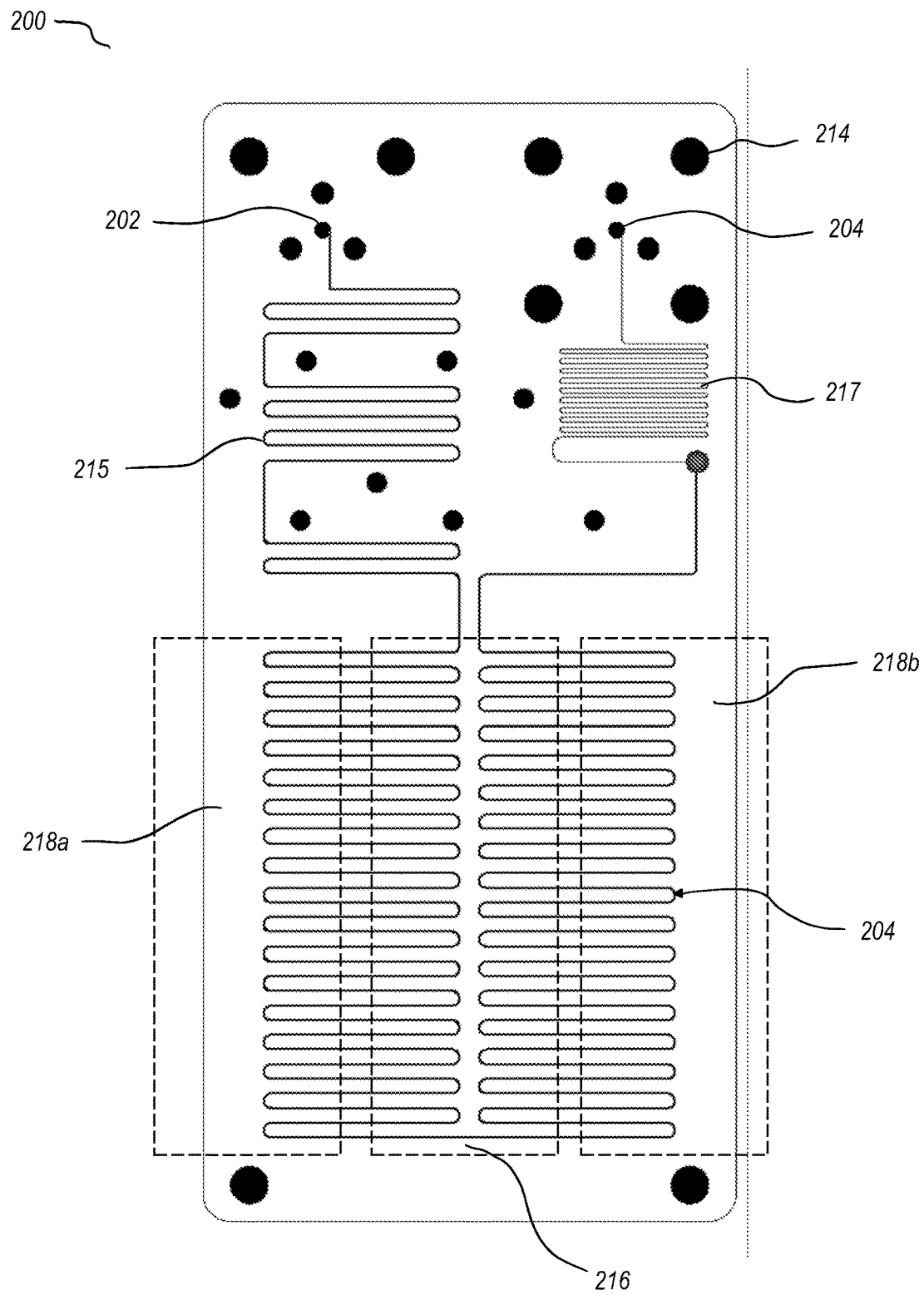
FIG. 7 illustrates another exemplary embodiment of a microfluidic card with a channel array arranged to make multiple longitudinal passes across the card.

FIG. 7 illustrates another embodiment of a microfluidic card 200 that may be utilized with a heating assembly as described above to provide rapid PCR. Except where noted otherwise, the card 200 may include features and components similar to those described above in relation to the card 100 and its associated components.

The card 200 includes a channel array 204 arranged with two longitudinal sections. As shown, the channel array 204 begins at the inlet 202, extends through a series of inlet turns 215, and then extends through multiple lateral sections that repeatedly pass through a hot zone 216 and a first cold zone 218*a*. After the first longitudinal section reaches the end of the card (opposite the inlet 202), the channel "doubles back" toward the inlet/outlet side of the card and makes additional lateral passes through the hot zone 216 and a second cold zone 218*b*.

This configuration beneficially provides the capability for multiple PCR cycles without requiring an overly large length-to-width ratio for the card 200. The card 200, for example, preferably has a length-to-width ratio of less than about 6, or more preferably less than about 4, or even more preferably less than about 3. The card 200 may, for example, have a length to width ratio of about 1 to 6, or about 1.5 to 5, or about 2 to 4. A length-to-width ratio within the foregoing ranges provides improved handleability and manufacturability of the card as compared to a larger length-to-width ratio. The inclusion of a second longitudinal section on the card 200 also beneficially allows both the inlet 202 and the outlet 204 components to be located on the same end of the card without the need for a long, non-cycling length of return channel.

The illustrated embodiment includes a single hot zone 216 disposed between two outer cold zones 218*a* and 218*b*. The heating assembly may be alternatively arranged with a single cold zone disposed between two outer hot zones or may even include more than three separate temperature zones for more granular PCR reaction schemes. Whatever their number or particular arrangement, the zones are arranged so that each lateral section of the channel array 204 passes through at least two temperature zones one "hot" for DNA denaturation and one "cold" for DNA annealing/extension.

The card 200 may also include one or more indexing features 214 similar to the card 100. The illustrated card also includes a set of outlet turns 217 disposed downstream of the active lateral sections of the temperature zones and upstream of the outlet 204. The outlet turns 217 may function similar to the inlet turns 215 by modulating and regulating the outlet flow prior to reaching the outlet 204.

Figure 8:
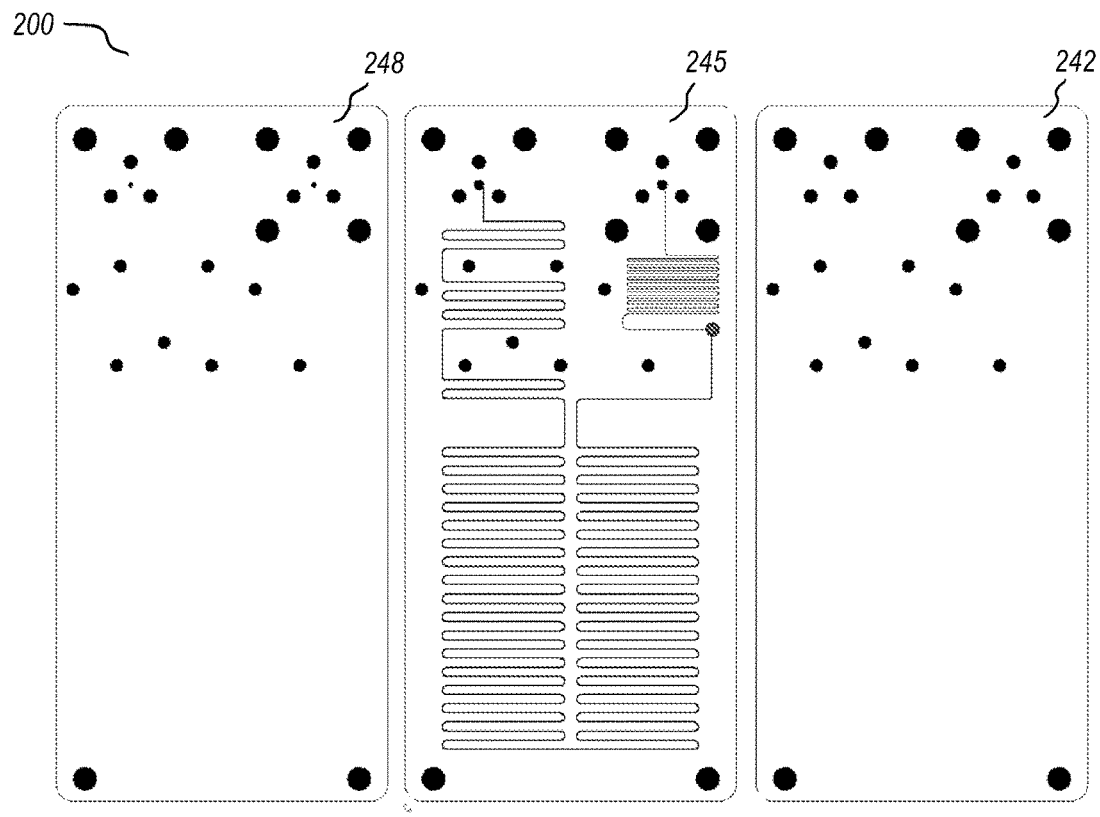
FIG. 8 illustrates the card of FIG. 7 in a layer-by-layer view.

FIG. 8 illustrates the card 200 in a layer-by-layer view. This embodiment includes a middle layer 245 formed between two outer layers 242 and 248. The outer layers 242 and 248 may be formed from a suitable polymer material, such as those described above in relation to card 100. In presently preferred embodiments, the outer layers 242 and 248 are formed of PET. Layers of PET provide good optical transparency and sufficient mechanical properties even at relatively thin thicknesses on the order of about 12 to 25 µl or less per layer.

The channel array components within the inner layer 245 may be formed through a suitable microfabrication process such as cutting and/or laser etching. Additionally, or alternatively, the channel array components may be formed using a photolithography process. For example, a polymer/epoxy film may be laminated to one of the outer layers, and the fluid channel geometry may then be removed from the film via photolithography. Presently preferred embodiments utilize a negative photoresist such as an SU-8 epoxy photoresist (i.e., Bisphenol A novolac epoxy dissolved in an organic solvent with up to 10 wt % mixed triarylsulfonium/hexafluoroantimonate salt); however, other embodiments may utilize a positive photoresist and/or other photoresist materials. Using a photolithography process, as opposed to a mechanical cutting process, beneficially provides greater dimensional control of the formed channels and better reproducibility of card structure.

Some card embodiments may additionally include one or more lanes for introducing PCR standards, such as a ladder, particular DNA concentration standards, cloned target sequences (e.g., circular and/or linearized plasmids), or other standards as known in the art.

The terms "approximately," "about," and "substantially" as used herein represent an amount or condition close to the stated amount or condition that still performs a desired function or achieves a desired result. For example, the terms "approximately," "about," and "substantially" may refer to an amount or condition that deviates by less than 10%, or by less than 5%, or by less than 1%, or by less than 0.1%, or by less than 0.01% from a stated amount or condition.

Elements described in relation to any embodiment depicted and/or described herein may be substituted for or combined with elements described in relation to any other embodiment depicted and/or described herein.

EXAMPLES

Example 1

Theoretical performance of thin films was compared against conventional microfluidic devices using a comparison of material properties and a numerical model. All of the analysis was done based on a simplified, one dimensional scenario in which heat transfers from copper to water (used to represent the reaction fluid) through a layer of polycarbonate.

Figure 9:
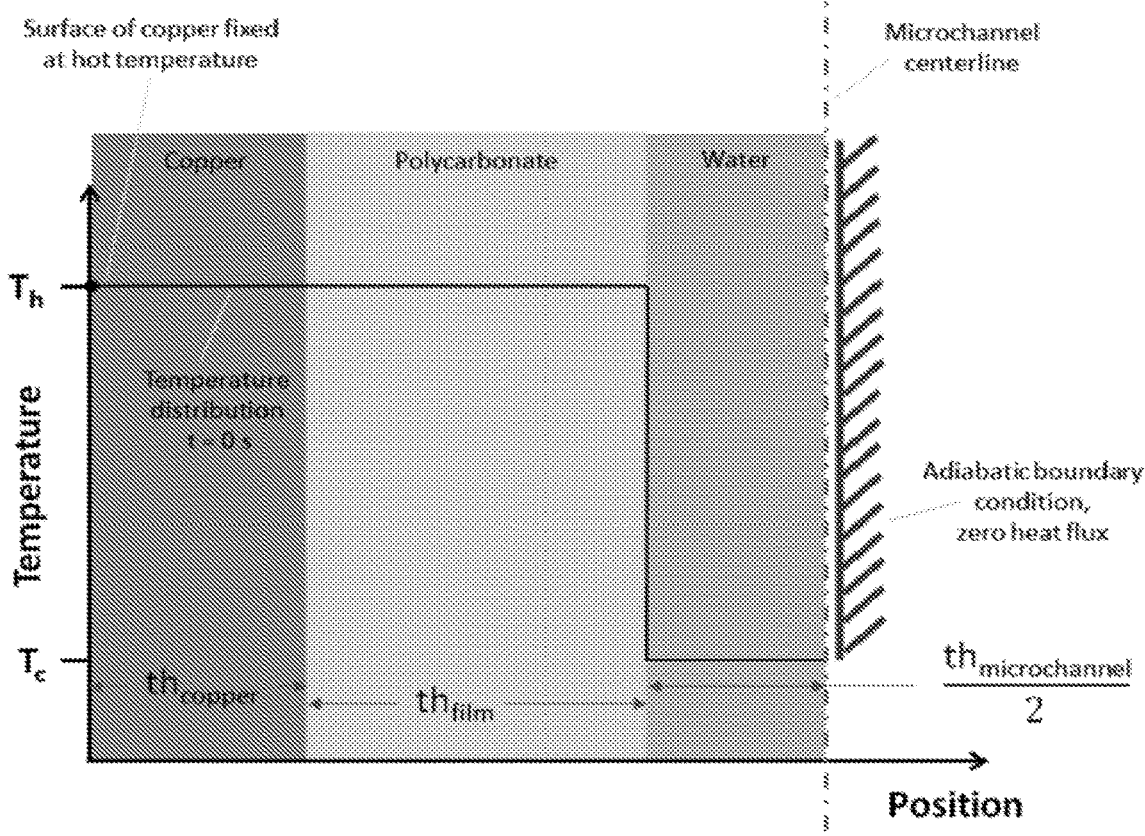
FIG. 9 illustrates boundary conditions used in a numerical simulation of heat transfer conditions.

A numerical model was developed to predict the time-dependent temperature distributions that occur in the fluid, polycarbonate, and copper when the fluid switches temperature zones. Since flow is laminar in a microfluidic channel, heat transfer within the fluid is largely due to conduction. As such, the system was modeled as 1-D conduction of a cold body of water equilibrating temperature with a layer of hot polycarbonate and hot copper. For simplicity, a symmetric half model was created by applying an adiabatic boundary condition to the centerline of the fluid (see FIG. 9).

For boundary conditions, the surface temperature of the copper is fixed at the hot temperature and heat flux is set to zero at the microchannel centerline. For initial conditions, the copper and polycarbonate temperatures are uniform at Th and the water temperature is uniform at $T_c$. The simulation tracks how the temperature distribution changes with time within each material given their thickness, denoted th.

Figure 10:
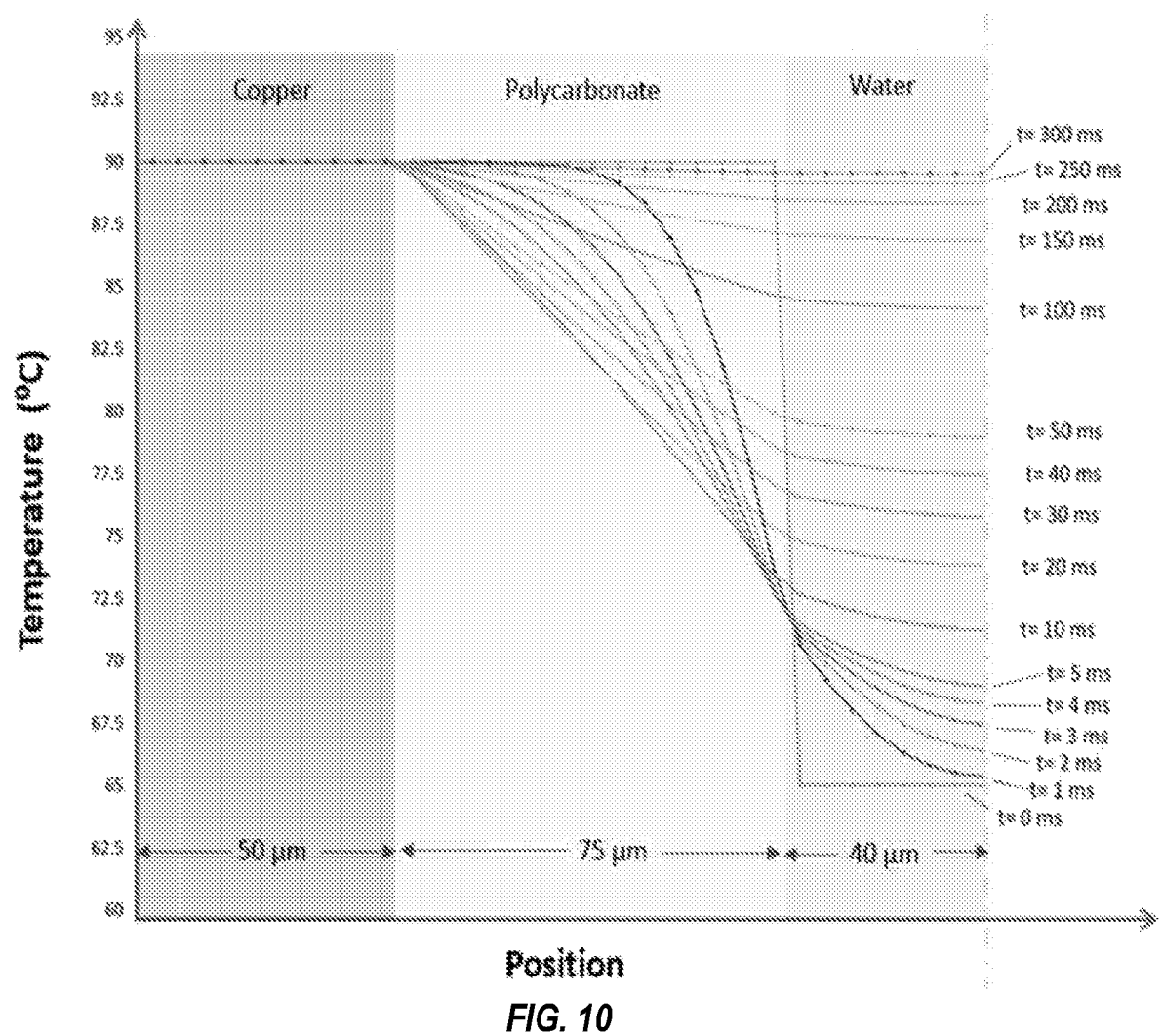
FIGS. 10 and 11 illustrate results of the numerical simulation for a thin film sample container (75 µm) and a bulk container (1 mm), respectively.

The simulation parameters were set to mimic the thin film PCR device. The fluid channel half-depth was set to 40 micrometers, the polycarbonate thickness to 75 micrometers, and the copper to 50 micrometers. The simulation shows that in the first 5 milliseconds, the polycarbonate-water interface temperature drops to 70 degrees Celsius (see FIG. 10). This agrees with the prediction that there will be a temperature gradient between the two materials and that the interface temperature will be closer to that of the water. After the initial drop, temperature equilibrates with the copper block. The temperature change in the copper block is negligible, as predicted.

Figure 11:
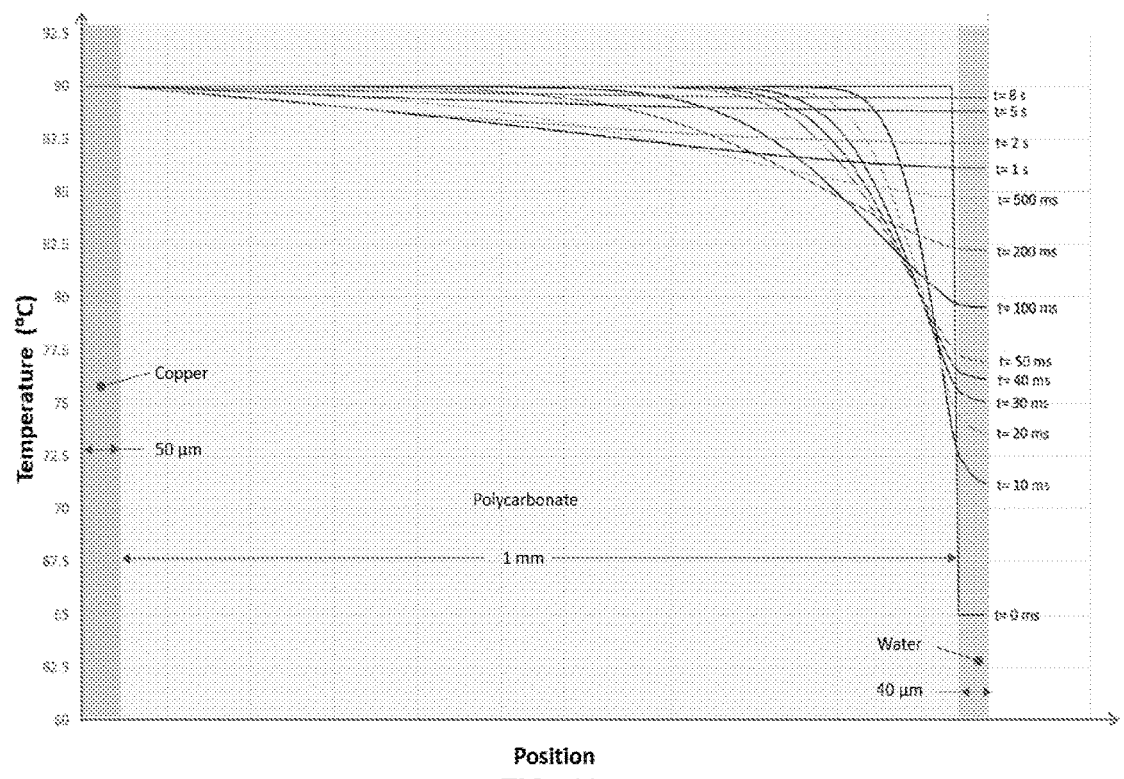

The simulation was run again with the wall thickness of the polycarbonate increased from 75 micrometers to 1 millimeter to compare thin film performance against a bulk sample container. The results reveal that significant temperature gradients linger in the sample container beyond the time scale required for extreme speeds (see FIG. 11). Qualitatively, the plastic cannot store and deliver enough heat to the water, and its thickness impedes heat transfer from the copper block.

Figure 12:
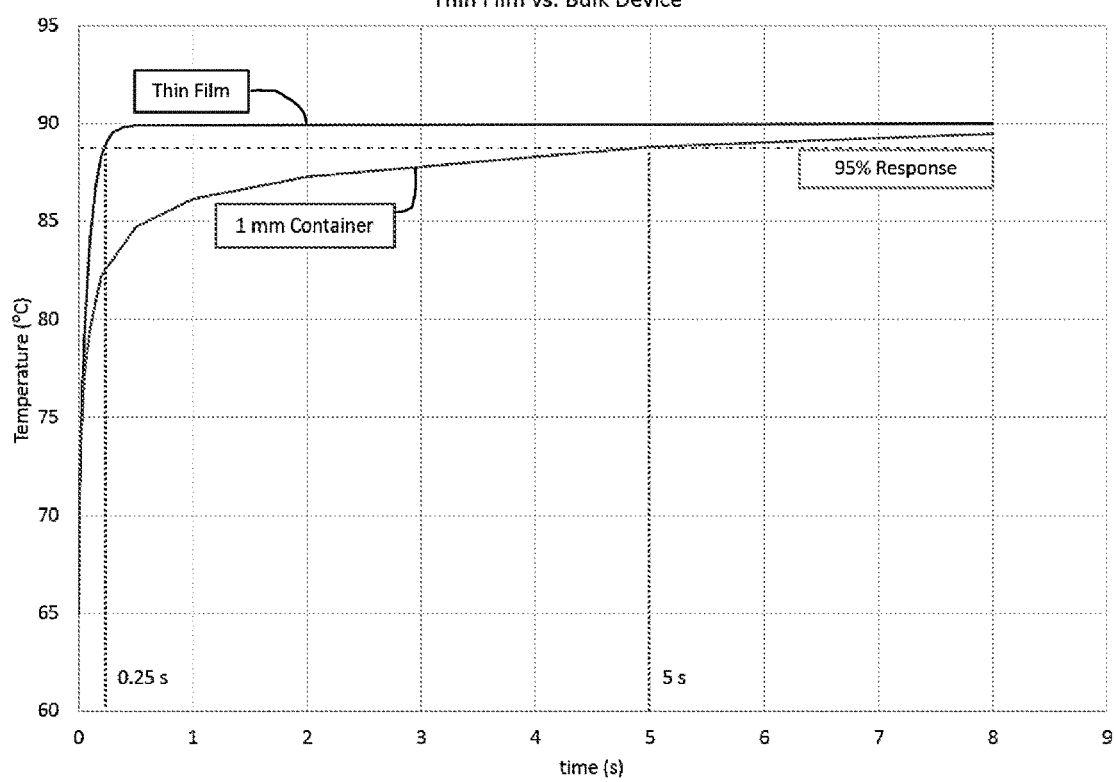
FIG. 12 shows the numerical simulation results for both the thin film and bulk sample containers.

The microchannel centerline is the furthest location from the copper block and therefore has the slowest temperature response. The temperature at the centerline vs. time was plotted and compared for both simulations (see FIG. 12). The 95% response time of the thin film was roughly 250 milliseconds, while that of the 1 millimeter container was approximately 5 seconds, or 20 times slower.

This analysis shows that success of the described system depends primarily on minimizing the distance between the PCR sample and the temperature source. Contact between sample fluid and a plastic container results in temperature gradients, and those gradients must be eliminated and equilibrated quickly in order to achieve extreme-speed temperature cycling.

Example 2

Amplification was performed on a 69 base pair target within a 450 base pair template of random sequence, synthetic DNA (Integrated DNA Technologies). Forward and Reverse primer lengths were 20 bases. To minimize primer-dimer formation prior to running PCR, the reaction was first prepared into a separate polymerase mix and a DNA/primer mix, both at double the final PCR concentration. The DNA/primer mix contained only the template and primers and the polymerase mix contained the remaining components. Prior to thermal cycling, 10 microliters of each were combined in a microfuge tube, and then 15 microliters were pipetted from the tube and run through the card, corresponding to a total template copy number of 31,500. Final reaction concentrations are shown in Table 1.

TABLE 1

Final PCR Concentrations

| Component | Concentration |
| --- | --- |
| Tris | 50 mM, pH 8.3 |
| MgCl$_2$ | 5 mM |
| each dNTP (dATP, dCTP, dGTP, dTTP) | 200 μM |
| nonacetylated BSA (Sigma) | 500 μg/mL |
| LCGreen ® Plus (BioFire Diagnostics) | 1X |
| Klentaq1 ™ DNA polymerase | 2 μM |
| Reaction Mix DNA | 2,100 copies/μL |
| Reaction Mix Forward Primer | 5 μM |
| Reaction Mix Reverse Primer | 5 μM |

The copper block pairs were set to temperatures of 90 and 65 degrees Celsius for the denaturation and annealing/extension temperature zones, respectively. The pressure regulator was set to 20.7 kilopascal (3 psi). An on-off valve was used to block pressure while the card was clamped into the instrument. The 15 μreaction mix was aspirated into a 20 microliter pipet tip, and then the tip, still containing liquid, was ejected into the card connector. After clamping the card, the valve was opened to begin thermal cycling.

Three negative controls with no template DNA and two positive controls were run on the instrument. Completed reactions were collected into the cap of a capillary tube (Light-Cycler Capillary, Roche Diagnostics), spun down, and high resolution melting was per-formed (HR-1, Biofire Diagnostics). For comparison, an identical reaction and negative control were run in parallel on the water bath system with the cycle time set to 1.2 seconds. A conventional PCR was also performed using polymerase and primer concentrations of 0.06 micromolar and 0.5 micromolar, respectively, with a cycle time of 15 seconds (Light Cycler, Roche Diagnostics).

Figure 13:
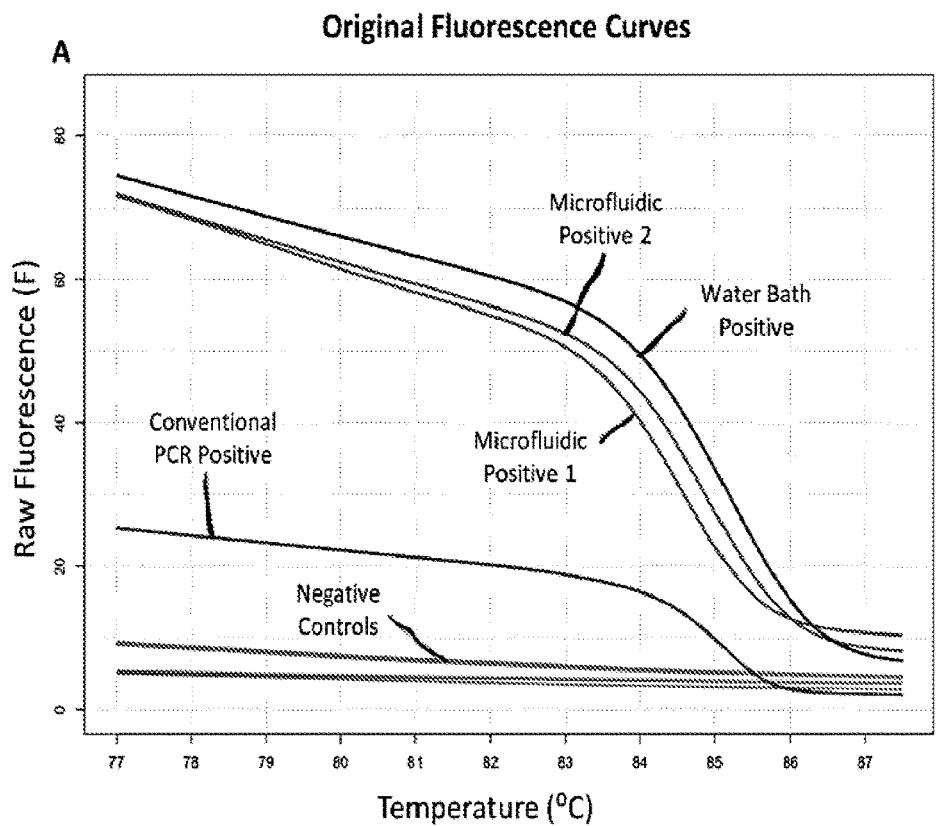
FIGS. 13 and 14 illustrates melting curves showing that DNA amplified in the rapid PCR system was similar to a positive control and showing that melting temperatures from experimental runs match the positive control and conventional PCR to within 1 degree Celsius.
Figure 14:
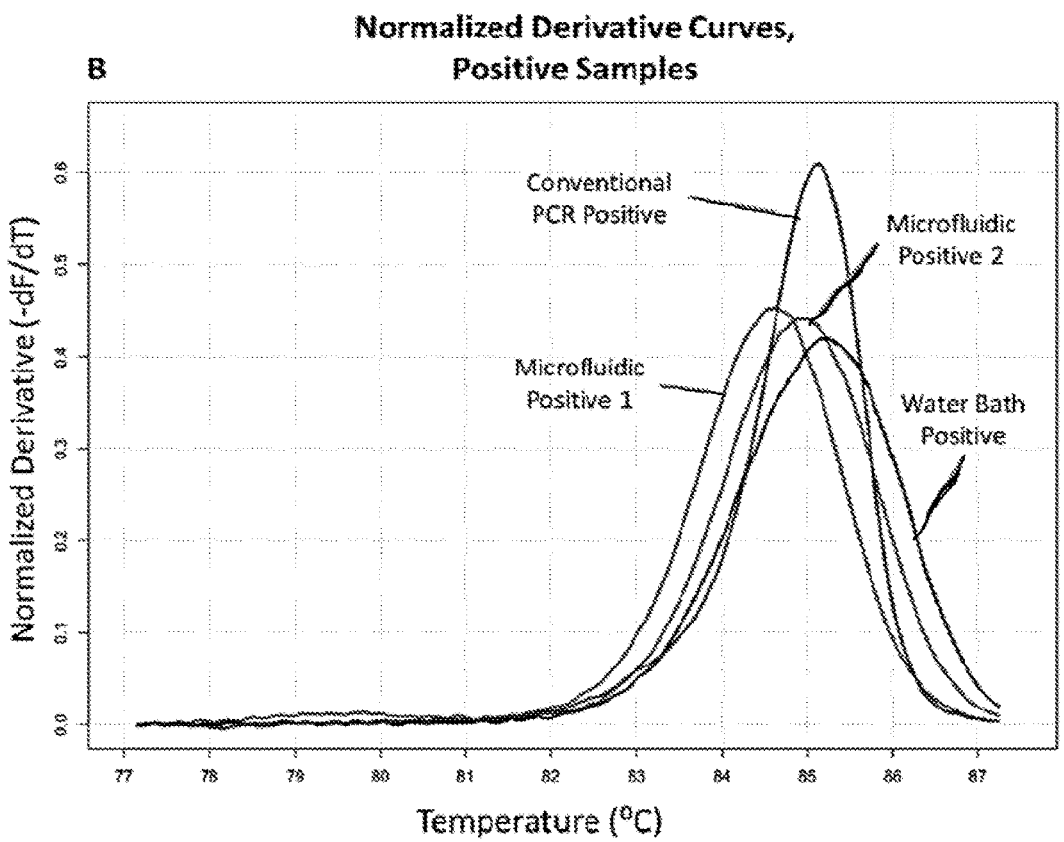

The system successfully amplified a 69-bp fragment of a 450-bp synthetic, random sequence dsDNA template. The fluid spent a total of approximately 52 seconds in the 35-cycle card including fluid entry and collection. The cycle time averaged 1.06 seconds. The original fluorescence melting curves show no amplification in the negative controls (see FIGS. 13 and 14). The melting curves of the positive controls and the water bath sample are similar in magnitude, indicating that the product concentration is similar. The normalized, negative derivative plot of the melting curves show that the melting temperatures match between all positive runs to within 1 degree Celsius, indicating that the specific DNA fragment was amplified. The size of the product was confirmed to be correct using an agarose gel.

The invention claimed is:

1. A microfluidic card configured for performing rapid PCR, the card comprising:
a longitudinal axis;
an upper surface;
a lower surface;
an inlet providing access to an internal channel;
the internal channel extending in a serpentine pattern to form a channel array comprising a plurality of sections oriented transverse to the longitudinal axis such that a fluid passing through the channel array passes through the lateral sections as it moves downstream of the inlet,
wherein the internal channel extends from a first end of a first end of the card toward a second end of the card to form a first longitudinal section of multiple lateral sections and reversing direction to extend back toward the first end of the card to form a second longitudinal section of multiple lateral sections.

2. The card of claim 1, wherein the card includes one or more alignment holes or marks for aligning the card with a heating assembly and/or pneumatic assembly.

3. The card of claim 1, wherein the card has a wall thickness between the channel array and the upper surface, and a wall thickness between the channel array and the lower surface, of less than 1 mm.

4. The card of claim 3, wherein the wall thickness is about 12.5 μm to about 300 μm.

5. The card of claim 1, wherein the inlet is configured for receiving a pipette tip.

6. The card of claim 5, wherein the inlet extends substantially perpendicularly from the upper surface of the card.

7. The card of claim 1, wherein the card is formed from a heat bondable thermoplastic.

8. The card of claim 1, wherein the card includes a photoresist inner layer positioned between outer polymer layers.

9. The card of claim 8, wherein the outer polymer layers are PET.

10. The card of claim 1, wherein the card has a length-to-width ratio of about 1 to 6, or about 1.5 to 5, or about 2 to 4.

11. A system configured for performing rapid PCR, the system comprising:
the microfluidic card of claim 1; and
a heating assembly configured such that the microfluidic card is positionable within the heating assembly, the heating assembly providing differential heat to different locations of the microfluidic card to generate the plurality of separate temperature zones when the card is positioned within and heated by the heating assembly,
wherein the heating assembly contacts the microfluidic card, when inserted, along both the upper surface and lower surface at least at each of the temperature zones.

12. The system of claim 11, wherein the channel array serpentine pattern winds repeatedly across the plurality of temperature zones to provide thermal cycling.

13. The system of claim 11, wherein the system has two temperature zones.

14. The system of claim 11, wherein the system has three or four temperature zones.

15. The system of claim 11, wherein the microfluidic card has a longitudinal axis, and wherein the temperature zones are oriented to be substantially parallel to the longitudinal axis.

16. The system of claim 11, further comprising a pneumatic assembly operatively couplable to the microfluidic card to provide a pressure differential for driving a reaction fluid through the channel array.

17. The system of claim 16, wherein the pneumatic assembly is coupled to the card inlet.

18. The system of claim 11, wherein the channel array includes a set of inlet turns disposed downstream of the inlet and upstream of the temperature zones to normalize fluid flow before entering the temperature zones.

19. The system of claim 11, wherein the heating assembly includes a plurality of heating blocks formed from copper and/or aluminum.

20. The system of claim 11, wherein the heating assembly includes at least two heating blocks per temperature zone, each temperature zone including at least one heating block adjacent to the upper surface of the microfluidic card and at least one corresponding heating block opposite the at least one heating block on the lower surface of the microfluidic card.

21. The system of claim 11, wherein the system is capable of PCR cycle times of about 5 seconds or less, about 3 seconds or less, about 2 seconds or less, or as low as about 0.5 to 1 second per cycle.

22. The system of claim 11, wherein the heating assembly includes an inner block associated with both the first and second longitudinal sections when the microfluidic card is positioned within the heating assembly, a first outer block is associated with the first longitudinal section when the microfluidic card is positioned within the heating assembly, and a second outer block is associated with the second longitudinal section when the microfluidic card is positioned within the heating assembly.

23. The system of claim 22, wherein the inner block is configured to form a temperature zone of a first temperature and wherein the outer blocks are each configured to form temperature zones of a second temperature.

24. A method of performing rapid PCR, the method comprising:
provinding the system of claim 11;
directing a PCR reaction mixture into the channel array of the microfluidic card as a fluid plug; and
the fluid plug traversing the channel array and being subjected to thermal cycling to enable rapid PCR.

25. The method of claim 24, wherein the PCR cycle time is about 5 seconds or less, about 3 seconds or less, about 2 seconds or less, or as low as about 0.5 to 1 second per cycle.

* * * * *